US011756403B2

(12) United States Patent
Hung (10) Patent No.: US 11,756,403 B2
(45) Date of Patent: Sep. 12, 2023

(54) CABINET WITH AED LIGHT SIGNAL DISPLAY

(71) Applicant: Sung-Ling Hung, New Taipei (TW)

(72) Inventor: Sung-Ling Hung, New Taipei (TW)

( * ) Notice: Subject to any disclaimer, the term of this patent is extended or adjusted under 35 U.S.C. 154(b) by 0 days.

(21) Appl. No.: 17/840,885

(22) Filed: Jun. 15, 2022

(65) Prior Publication Data

US 2022/0406162 A1 Dec. 22, 2022

(30) Foreign Application Priority Data

Jun. 21, 2021 (TW) ................................ 110122633

(51) Int. Cl.
| | | |
|---|---|---|
| *G08B 21/18* | (2006.01) | |
| *G08B 5/36* | (2006.01) | |
| *A61N 1/39* | (2006.01) | |

(52) U.S. Cl.
CPC ........... *G08B 21/18* (2013.01); *A61N 1/3904* (2017.08); *G08B 5/36* (2013.01)

(58) Field of Classification Search
CPC .... A61B 5/11; A61N 1/37282; A61N 1/3931; A61N 1/3993; A61N 1/3904; G01R 31/392; G08B 5/36; G08B 13/19619; G08B 21/18; H01Q 1/243; H02J 9/02; H04B 1/0406; H04B 1/109
USPC ...................................................... 340/815.4
See application file for complete search history.

(56) References Cited

U.S. PATENT DOCUMENTS

| | | | | |
|---|---|---|---|---|
| 4,551,714 | A * | 11/1985 | Giammarese | .......... H04B 1/202 340/4.62 |
| 4,962,473 | A * | 10/1990 | Crain | ..................... G08B 19/00 340/539.2 |
| 2006/0149321 | A1* | 7/2006 | Merry | .................. A61N 1/3904 607/60 |
| 2006/0250271 | A1* | 11/2006 | Zimmerman | ............ G08B 5/22 340/8.1 |
| 2008/0132090 | A1* | 6/2008 | Bozzone | .............. H01R 12/718 439/38 |
| 2010/0233889 | A1* | 9/2010 | Kiani | ................... A61B 5/6826 439/38 |
| 2012/0130534 | A1* | 5/2012 | Wurm | ................ G07F 17/0092 700/236 |
| 2013/0064622 | A1* | 3/2013 | Mekid | ..................... F16B 31/02 411/13 |
| 2018/0054695 | A1* | 2/2018 | Castor | ................ H04W 68/005 |

(Continued)

FOREIGN PATENT DOCUMENTS

| | | |
|---|---|---|
| TW | M529513 U | 10/2016 |
| TW | M617877 U | 10/2021 |

*Primary Examiner* — Stephen R Burgdorf
(74) *Attorney, Agent, or Firm* — Muncy, Geissler, Olds & Lowe, P.C.

(57) ABSTRACT

A cabinet with AED light signal display is disclosed. A cabinet body receives an AED having an indicator. A light signal indication device is disposed on the outside of the cabinet body. A status sensor is disposed on the outside of the indicator of the AED and is electrically connected to the circuit board through a transmission cable, detecting a display status of the indicator of the AED to generate a detection result. A circuit board is electrically connected to the status sensor and a light signal indication device. The circuit board generates a control signal according to the detection result, controlling the light signal indication device to show a light signal corresponding to the indicator.

10 Claims, 5 Drawing Sheets

(56) References Cited

U.S. PATENT DOCUMENTS

| | | | | |
|---|---|---|---|---|
| 2018/0249563 A1* | 8/2018 | Alexander | ............... | F21V 14/02 |
| 2018/0340843 A1* | 11/2018 | Tsai | ........................ | E03C 1/04 |
| 2020/0406047 A1 | 12/2020 | Malott | | |
| 2021/0074417 A1* | 3/2021 | Pierson | ................... | H04L 67/34 |
| 2021/0075268 A1* | 3/2021 | Stever | ..................... | H02J 50/80 |
| 2021/0228893 A1* | 7/2021 | Akram | ................. | A61N 1/3904 |

\* cited by examiner

CABINET WITH AED LIGHT SIGNAL DISPLAY

This application claims priority of Application No. 110122633 filed in Taiwan on 21 Jun. 2021 under 35 U.S.C. § 119; the entire contents of all of which are hereby incorporated by reference.

BACKGROUND OF THE INVENTION

Field of the Invention

The invention relates to a cabinet, and more particularly to a cabinet with AED light signal display.

Description of the Prior Art

An AED (Automated External Defibrillator) is a portable first-aid device provided for non-medical personnel in case of cardiac arrest. In sudden cardiac arrest caused by sudden arrhythmia, if the heart is given an electric shock within one minute, the success rate of first-aid for the heart may be as high as 90%, and it gradually decreases over time. Accordingly, the survival rate of patients is a race against time. If the AEDs are provided in crowded public areas for use in rescue, the pre-hospital mortality from such patients can be reduced.

An indicator is usually disposed on the corner of the housing of the AED, showing the power condition. There are many types of indicators, and the types vary by brand. For example, green light, blacklight, or a circle symbol may be referred to as power on, while red light, white light, or a cross symbol referred to as power off. Although conventional cabinets for receiving the AED are provided with transparent glass, the visibility of the indicator on the AED is still insufficient, such that the green light, the red light, the blacklight, the white light, the circle symbol, or the cross symbol cannot be clearly observed. Accordingly, the AED may not be usable in the event of an emergency, causing irreversible results to the patients.

Hence, there is a need for a cabinet with AED light signal display to overcome the aforementioned problems effectively.

SUMMARY OF THE INVENTION

An object of the invention is to provide a cabinet with AED light signal display. A status sensor detects a status of an indicator on an AED. The status is transmitted to a light signal indication device disposed on the outside of a cabinet body through a circuit board. Thus, even when the AED is located in the cabinet body and is separated by a door plate, the status of the AED can be observed by way of the light signal indication device. Additionally, the AED can be instantly handled with appropriate measures when it is out of power or parts of it need to be replaced.

Another object of the invention is to provide a cabinet with an AED light signal display. A plurality of RFID sensors is disposed in a cabinet body. For monitoring and managing, a plurality of RFID labels is disposed on first-aid items, such as an AED and a first-aid medicine.

Another object of the invention is to provide a cabinet with an AED light signal display. An alarm display panel is disposed on a cabinet body and displays an area plan displaying a plurality of alert lights respectively corresponding to the actual positions of a plurality of alarm transmitters. When any one of the alarm transmitters is activated, an alert light corresponding thereto emits light. Thus, neighboring personnel can intuitively find out the location of an incident and immediately go to the location with an AED, saving the time of searching for the alarm transmitter.

An exemplary embodiment of the invention provides a cabinet with AED light signal display, comprising a cabinet body, a light signal indication device, a status sensor, and a circuit board. The cabinet body receives an AED having an indicator. The light signal indication device is disposed on the outside of the cabinet body. The status sensor is disposed on the outside of the indicator of the AED, detecting a display status of the indicator of the AED to generate a detection result. The circuit board is electrically connected to the status sensor and light signal indication device. The circuit board generates a control signal according to the detection result, controlling the light signal indication device to show a light signal corresponding to the indicator.

According to an embodiment of the invention, the status sensor comprises a chip and an attachment area covering the chip and overlaying the indicator of the AED.

According to an embodiment of the invention, the cabinet body accommodates a first electrical contact electrically connected to the circuit board. The status sensor is connected to a second electrical contact through a transmission cable. The second electrical contact is electrically connected to the first electrical contact, transmitting the detection result generated by the status sensor to the circuit board through the first and second electrical contacts. The circuit board converts the detection result into the control signal and transmits the control signal to the light signal indication device.

According to an embodiment of the invention, the first and second electrical contacts are connected to each other by magnetic attraction.

According to an embodiment of the invention, the cabinet with AED light signal display further comprises a wireless signal transceiver connected to the circuit board and signally connected to a backend monitoring server.

According to an embodiment of the invention, the cabinet body comprises a wireless signal transmission area. At least one signal received by the wireless signal transceiver is output to the exterior of the cabinet body through the wireless signal transmission area when the wireless signal transceiver is disposed in the cabinet body.

According to an embodiment of the invention, a door sensor is disposed on an inner side of a door plate of the cabinet body and is connected to the circuit board. The circuit board outputs a notification message to the backend monitoring server when the door sensor detects opening of the door plate.

According to an embodiment of the invention, an alarm display panel is disposed on the cabinet body and displays an area plan displaying a plurality of alert lights respectively corresponding to the actual positions of a plurality of alarm transmitters. When any one of the alarm transmitters is activated, an alert signal output therefrom is received by the wireless signal transceiver. The circuit board activates the alarm display panel, enabling the alert light corresponding to the alarm transmitter to emit light.

According to an embodiment of the invention, the circuit board is further connected to at least one RFID sensor. At least one RFID label is disposed on the AED. The RFID sensor reads the content of the RFID label.

According to an embodiment of the invention, the cabinet body further accommodates at least one first-aid medicine on which the RFID label is disposed. The RFID sensor is disposed at the first-aid medicine, reading the content of the RFID label.

According to an embodiment of the invention, the circuit board is further connected to a temperature and humidity sensor detecting the temperature and humidity in the cabinet body and transmitting the same to the backend monitoring server through the wireless signal transceiver.

According to an embodiment of the invention, the circuit board is further connected to an audio sensor detecting a sound in the cabinet body and transmitting a signal of the sound to the backend monitoring server through the wireless signal transceiver.

According to an embodiment of the invention, a carbon monoxide sensor is disposed in the exterior of the cabinet body and outputs an alert sound when a carbon monoxide concentration detected thereby exceeds a predetermined level. The audio sensor detects the alert sound and transmits a signal corresponding thereto to the backend monitoring server.

According to an embodiment of the invention, the cabinet body further comprises a power module electrically connected to power mains and the circuit board. The power mains power the circuit board through the power module. The power module outputs electric power in the event of a power failure.

DESCRIPTION OF THE PREFERRED
EMBODIMENTS

Reference will now be made in detail to embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, methods and apparatus in accordance with the present disclosure. It is to be understood that elements not specifically shown or described may take various forms well known to those skilled in the art. Many alternatives and modifications will be apparent to those skilled in the art, once informed by the present disclosure.

The invention provides a cabinet with AED light signal display. The cabinet receives an AED (Automated External Defibrillator). A light signal indication device disposed on the outside of a cabinet body synchronously displays a light change of the AED, promoting visibility thereof. Thus, the AED can be charged, batteries thereof can be replaced, or contents thereof can be renewed in advance, preventing failure thereof in case of an emergency.

Referring to FIGS. 1-4, a cabinet with AED light signal display, according to an embodiment of the invention, comprises a cabinet body 12, an AED 14, a status sensor 20, a light signal indication device 22, and a circuit board 16. The AED 14 is received in the cabinet body 12. In this embodiment, the cabinet body 12 includes a top layer and a bottom layer receiving the AED 14. The circuit board 16 is disposed in the cabinet body 12. The cabinet body 12 comprises a door plate 122. The light signal indication device 22 is disposed on the outside of the cabinet body 12. In the embodiment shown in FIGS. 1-3, the light signal indication device 22 is disposed on the outside of the door plate 122. An indicator 144 showing statuses is disposed on the AED 14. The indicator 144 may be an indication board or an indication lamp showing colors or graphics. The status sensor 20 is disposed on the outside of the indicator 144 and is electrically connected to the circuit board 16 through a transmission cable 202. The status sensor 20 may be a color sensor or a graphic sensor, detecting the display status, such as the color or graphic, of the indicator 144, thereby generating a detection result. The detection result is then transmitted to the circuit board 16 through the transmission cable 202. The circuit board 16 generates a control signal capable of controlling the light signal indication device 22 according to the detection result and transmits the control signal to the light signal indication device 22. Then, the light signal indication device 22 synchronously displays a light signal corresponding to or the same as that displayed by the indicator 144. For example, when the indicator 144 displays green light, a circle symbol, or other colors or graphics representing a normal status, the circuit board 16 outputs the control signal to enable the light signal indication device 22 to display the corresponding light, such as the green light. On the other hand, when the indicator 144 displays red light, a cross symbol, or other colors or graphics representing an abnormal status, the circuit board 16 outputs the control signal to enable the light signal indication device 22 to display the corresponding light, such as the red light.

Figure 5:
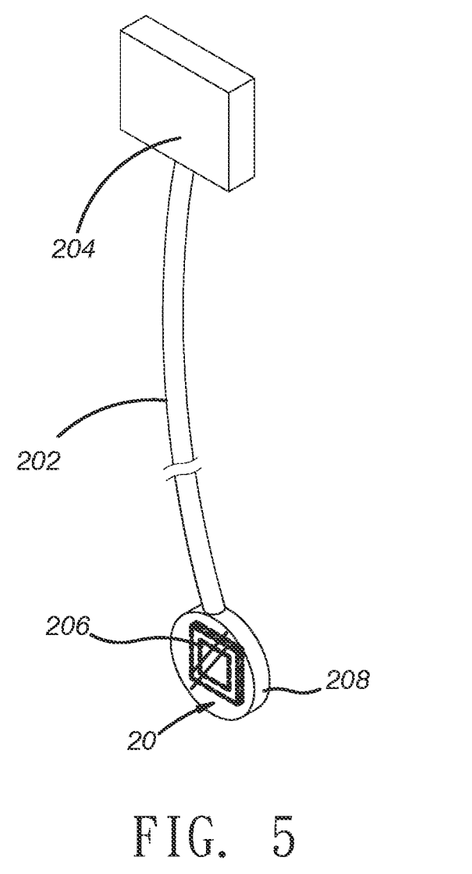
FIG. 5 is a schematic view showing a status sensor connected to a transmission cable and a second electrical contact according to an embodiment of the invention.

As shown in FIG. 5, the status sensor 20 comprises a chip 206 and an attachment area 208 covering the chip 206. The chip 206 is a sensing chip of the status sensor 20, identifying the colors or graphics displayed by the indicator 144. The attachment area 208 is transparent, allowing the chip 206 to detect the colors or graphics displayed by the indicator 144. The status sensor 20 may overlay the indicator 144 of the AED 14 by means of adsorption, attachment, adhesion, embedding, etc. For example, the status sensor 20 may be fixed to the indicator 144 by a felt or tape. In an embodiment, a light-emitting element (not shown) is disposed on the status sensor 20, persistently and weakly illuminating the indicator 144. When the color or graphic displayed by the indicator 144 is changed, an image is immediately captured and calculated. For example, if the normal or abnormal status of the AED 14 is indicated by a variation of the color (such as red/green or black/white) displayed by the indicator 144, the chip 206 in the status sensor 20 can analyze what color is currently displayed by the indicator 144 using the spectral bands of different colors. If the normal or abnormal status of the AED 14 is indicated by a variation of the graphic (such as a circle symbol, a cross symbol, or other graphics) displayed by the indicator 144, the chip 206 in the status sensor 20 can be loaded with image recognition algorithms (such as edge computing or other methods) to figure out the graphic the indicator 144 is displaying.

Nevertheless, one end of the transmission cable 202 is connected to the status sensor 20, while the other is connected to the circuit board 16. When the AED 14 is taken out, there is no time to remove the status sensor 20 due to an emergent condition. The status sensor 20 or transmission cable 202 may be easily damaged because of directly pulling. Accordingly, the cabinet body 12 accommodates a first electrical contact 222 fixed to an inner surface thereof and electrically connected to the circuit board 16. The other end of the transmission cable 202 connected to the status sensor 20 is provided with a second electrical contact 204 connected to the first electrical contact 222. Specifically, the first electrical contact 222 is connected to the second electrical contact 204 by magnetic attraction. Thus, the first electrical contact 222 can be easily detached from the second electrical contact 204 by slightly pulling the AED 14. The AED 14 can then be taken out together with the status sensor 20.

Accordingly, the status sensor 20 transmits the detection result of the indicator 144 to the second electrical contact 204 through the transmission cable 202. The detection result is then transmitted from the first electrical contact 222 to the circuit board 16. The circuit board 16 generates a control signal according to the detection result and transmits the control signal to the light signal indication device 22.

The circuit board 16 is signally connected to a backend monitoring server 30 in a wired or wireless manner. When the circuit board 16 transmits signals by way of the wireless manner, the cabinet with an AED light signal display, according to the invention, further comprises a wireless signal transceiver 162. The wireless signal transceiver 162 may be Wi-Fi or radio and is disposed in the interior or exterior of the cabinet body 12. The wireless signal transceiver 162 is signally connected to the backend monitoring server 30, transmitting various detection signals received by the circuit board 16 to the backend monitoring server 30. Additionally, the cabinet body 12 is made of metal and thus blocks wireless signal transmission. When the wireless signal transceiver 162 is disposed in the cabinet body 12, a wireless signal transmission area 124 (e.g., a window made of non-metals, such as an acrylic and plastic plate) is disposed on the cabinet body 12 to enable the wireless signal transceiver 162 to transmit and receive wireless signals. In the embodiment shown in FIGS. 1-3, the wireless signal transmission area 124 is disposed right on the top of the cabinet body 12.

Figure 4:
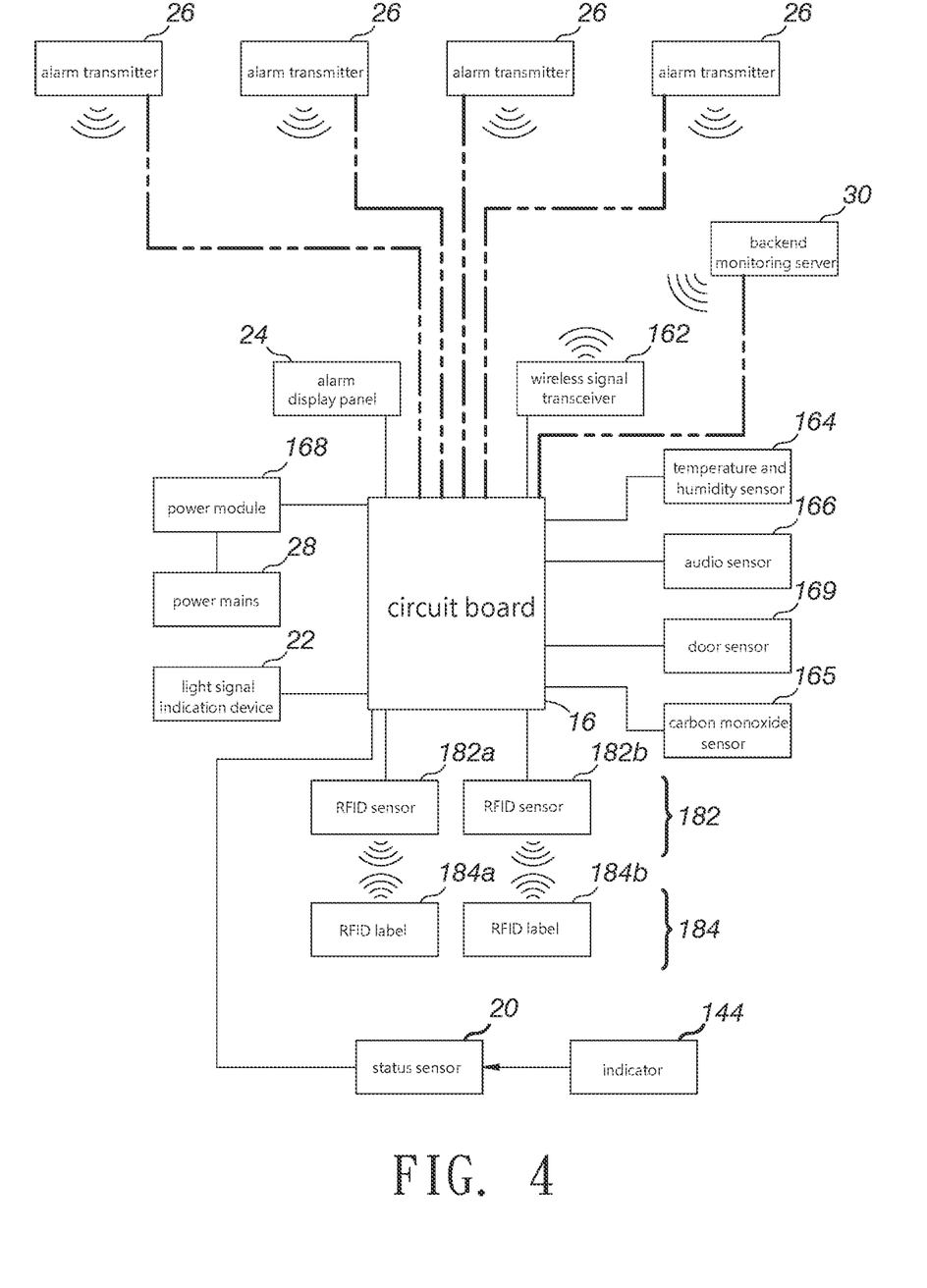
FIG. 4 is a circuit block diagram of a cabinet with an AED light signal display according to an embodiment of the invention.

The invention may include a variety of sensors, such as a temperature and humidity sensor 164, a carbon monoxide sensor 165, an audio sensor 166, and a door sensor 169. The temperature and humidity sensor 164 is disposed in the cabinet body 12 and is electrically connected to the circuit board 16, detecting the temperature and humidity in the cabinet body 12 and transmitting the same to the backend monitoring server 30 through the wireless signal transceiver 162 or a network cable. The carbon monoxide sensor 165 is disposed in the exterior of the cabinet body 12. The audio sensor 166 is disposed in the cabinet body 12 and is electrically connected to the circuit board 16. The carbon monoxide sensor 165 outputs an alert sound when a carbon monoxide concentration exceeding a predetermined level is detected. The audio sensor 166 detects the alert sound and transmits a signal corresponding thereto to the backend monitoring server 30 through the wireless signal transceiver 162 or network cable, notifying monitoring personnel to pay attention. The door sensor 169 is disposed on the inner side of the door plate 122, e.g., a position adjacent to a doorknob, and is connected to the circuit board 16. When detecting the opening of the door plate 122, the door sensor 169 outputs a signal to the circuit board 16. The circuit board 16 then transmits a notification message to the backend monitoring server 30 through the wireless signal transceiver 162 or network cable, notifying the monitoring personnel of the opening of the cabinet.

Figure 1:
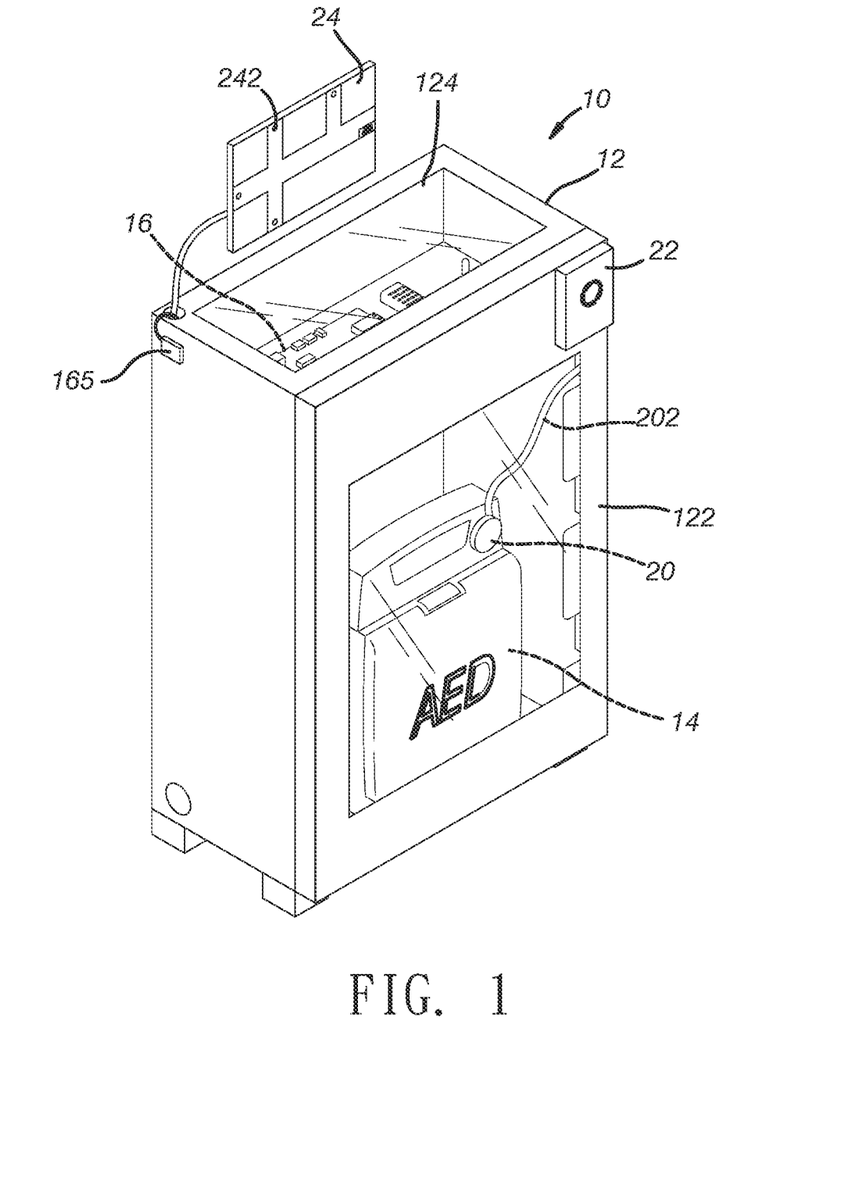
FIG. 1 is a schematic view showing a cabinet with an AED light signal display according to an embodiment of the invention.
Figure 2:
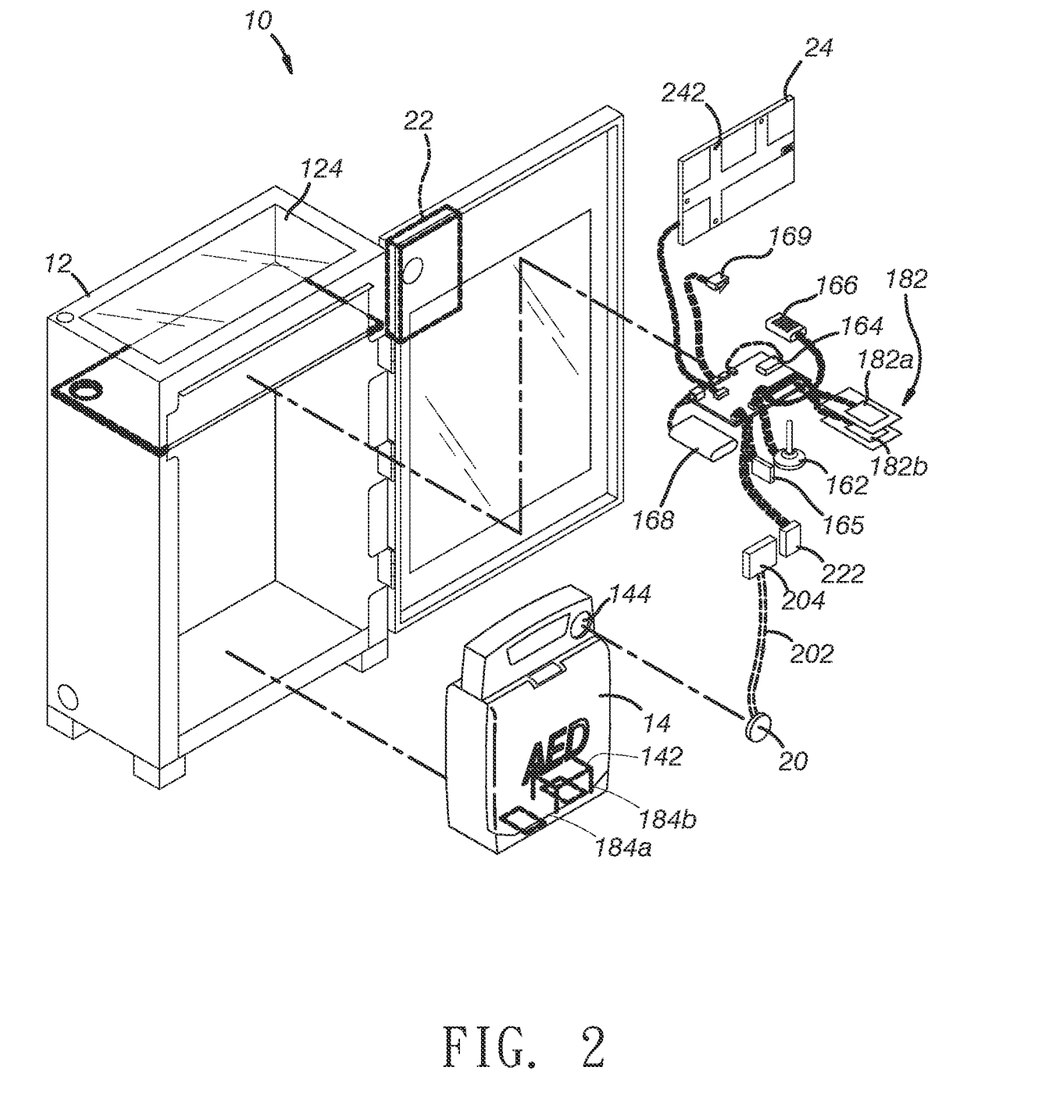
FIG. 2 is an exploded view showing a cabinet with an AED light signal display according to an embodiment of the invention.
Figure 3:
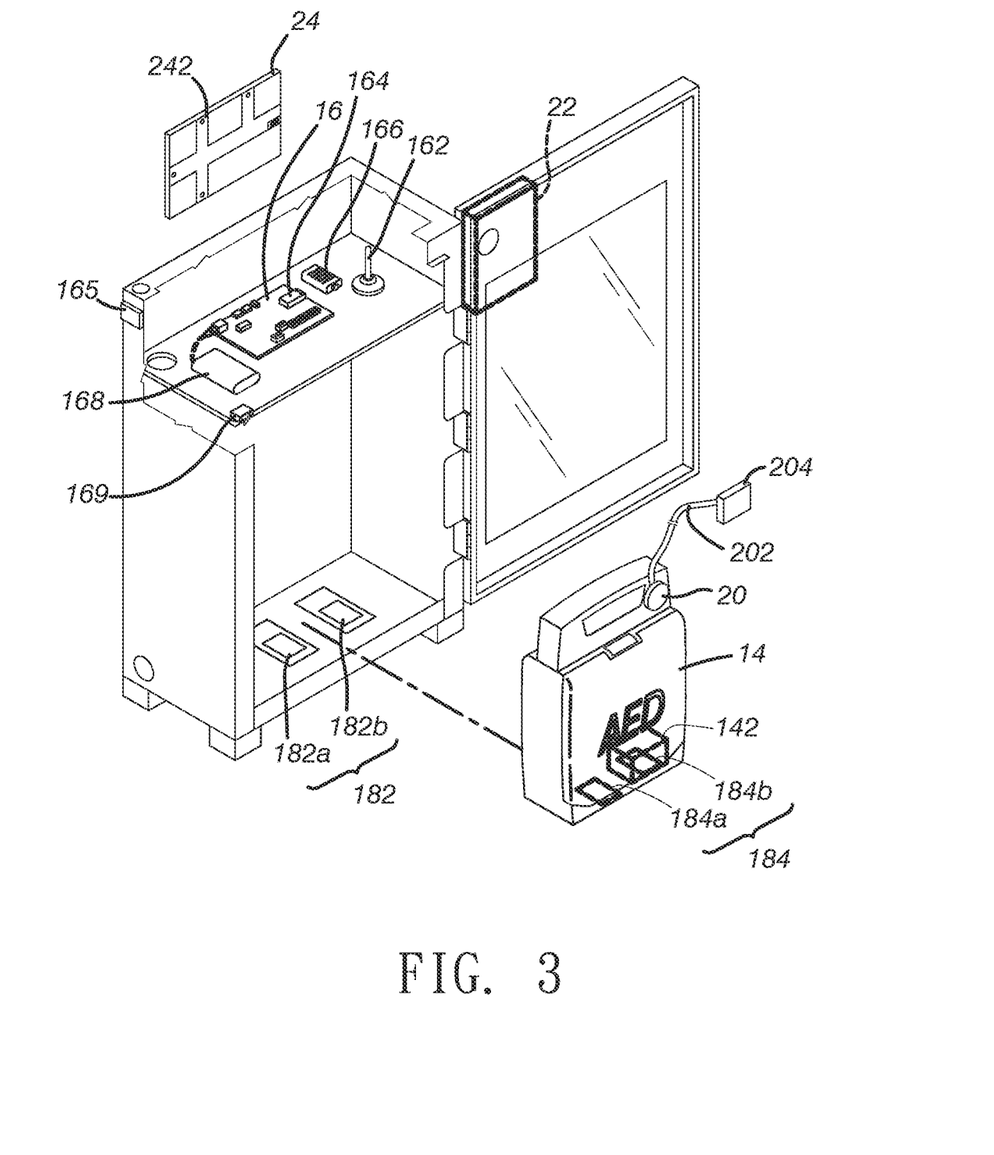
FIG. 3 is another exploded view showing a cabinet with an AED light signal display according to an embodiment of the invention.

Moreover, the invention utilizes the radio frequency identification (RFID) technique to record the information of various first-aid items in the cabinet body 12. The circuit board 16 is connected to at least one RFID sensor 182, and at least one RFID label is attached to the item that needs to be recorded. As shown in FIG. 3, an RFID label 184a is attached to the AED 14, and another RFID label 184b is attached to a battery of the AED 14. RFID sensors 182a and 182b are respectively disposed in the cabinet body 12. To simplify the drawing figure, connection cables between the RFID labels 184a and 182b and the circuit board 16 are omitted. The RFID sensors 182a and 182b read the contents (e.g., the replacement date and times of use of a battery 142, and the used times, manufacture date, and model number of the AED 14) of the RFID labels 184a and 182b, respectively. The cabinet body 12 further accommodates at least one first-aid medicine (not shown), such as Diphoterine, Hexafluorine, etc. For example, Diphoterine may be applied to a wounded area of a patient when corrosive or irritant chemicals sputter the skin thereof. It is preferred to use the aforementioned first-aid medicines as soon as possible. For example, when the eyes of the patient are sputtered by the corrosive or irritant chemicals, the first-aid medicines must be applied thereto within 10 to 60 seconds. Thus, it is preferred that the first-aid medicines are arranged in the AED 14 for quick access. Nevertheless, the aforementioned first-aid medicines are expensive. For example, the price of 100 ml of Diphoterine exceeds NT$ 3,000. To prevent the loss of the first-aid medicines, each RFID label is disposed on each first-aid medicine, and each RFID sensor is disposed at the same. Accordingly, by reading the content of the RFID label, the name, usage, and shelf life of each first-aid medicine can be acquired.

Furthermore, when the AED 14 or first-aid medicines are removed from the cabinet body 12, the RFID sensor 182 outputs a signal to the circuit board 16, and the circuit board 16 transmits a notification message to the backend monitoring server 30 through the wireless signal transceiver 162, informing the monitoring personnel that a certain or several first-aid items have been consumed. When the first-aid medicines are used up, the RFID sensor 182 outputs a signal to the backend monitoring server 30, informing the monitoring personnel to replenish the first-aid medicines.

In one embodiment of the invention, the circuit board 16 and sensors connected thereto are connected to a power module 168 to acquire electric power. The power module 168 is connected to power mains 28. The power mains 28 power the circuit board 16 through the power module 168. The power module 168 outputs electric power in the event of a power failure.

An alarm display panel 24 is further disposed on the cabinet body 24. The alarm display panel 24 may be made of plastics, acrylics, or other materials. An area plan is presented on the alarm display panel 24 by means of printing, drawing, or other manners. For example, when each AED 14 is disposed in each floor of a building, the area plan is referred to as the plan view of the floor. The area plan displays the positions of both the cabinet 10 with an AED light signal display and a plurality of alarm transmitters 26. The area plan displays a plurality of alert lights 242 respectively corresponding to the actual positions of the alarm transmitters 26. The alert lights 242 are electrically connected to the circuit board 16. When any one of the alarm transmitters 26 is activated, an alert signal, wired or wireless, is output therefrom. The alert signal is received by the circuit board 16 when it is wired. On the other hand, the alert signal is received by the wireless signal transceiver 162 when it is wireless. The alert light 242 corresponding to the alarm display panel 24 is then powered on by the circuit board 16. Accordingly, wherever needs first-aid, the personnel on the scene of the incident can press the alarm transmitter 26, and the alert light 242 corresponding to the cabinet 10 with an AED light signal display can then be powered on to emit light. The personnel around the cabinet 10 can easily sight the location of the incident scene from the alarm display panel 24 and immediately bring the AED 14 to the incident scene, saving the time for rescuing.

Moreover, the alarm display panel 24 may be a display screen displaying the area plans of all areas and the positions of the cabinet 10 and alarm transmitters 26. When any one of the alarm transmitters 26 is activated, the alert signal output therefrom is received by the wireless signal transceiver 162 or circuit board 16, activating the alarm display panel 24, and thereby enabling the alert light 242 of the alarm transmitters 26 to emit light.

While the invention has been described by way of example and in terms of the preferred embodiment, it is to be understood that the invention is not limited thereto. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A cabinet with AED light signal display, comprising:
a cabinet body receiving an AED having an indicator;
a light signal indication device disposed on the outside of the cabinet body;
a status sensor disposed on the outside of the indicator of the AED, detecting a display status of the indicator of the AED to generate a detection result;
a circuit board electrically connected to the status sensor and light signal indication device, wherein the circuit board generates a control signal according to the detection result, controlling the light signal indication device to show a light signal corresponding to the indicator; and
a first electrical contact accommodated in the cabinet body and electrically connected to the circuit board, the first electrical contact is further electrically connected with a second electrical contact, the status sensor is connected to the second electrical contact through a transmission cable, wherein the detection result generated by the status sensor is transmitted to the circuit board through the second electrical contact and the first electrical contact, and the circuit board converts the detection result into the control signal and transmits the control signal to the light signal indication device;
wherein the first electrical contact and the second electrical contact are connected by magnetic attraction;
wherein the circuit board is further connected to at least one RFID sensor, at least one first RFID label is disposed on the AED, and the at least one RFID sensor reads a content of the at least one first RFID label, wherein the cabinet body further accommodates at least one first-aid medicine on which a second RFID label is disposed, and the at least one RFID sensor is disposed at the at least one first-aid medicine, reading a content of the second RFID label.

2. The cabinet with AED light signal display as claimed in claim 1, wherein the status sensor comprises a chip and an attachment area covering the chip and overlaying the indicator of the AED.

3. The cabinet with AED light signal display as claimed in claim 1, further comprising a wireless signal transceiver connected to the circuit board and signally connected to a backend monitoring server.

4. The cabinet with AED light signal display as claimed in claim 3, wherein the cabinet body comprises a wireless signal transmission area, and at least one signal received by the wireless signal transceiver is output to the exterior of the cabinet body through the wireless signal transmission area when the wireless signal transceiver is disposed in the cabinet body.

5. The cabinet with AED light signal display as claimed in claim 3, wherein a door sensor is disposed on an inner side of a door plate of the cabinet body and is connected to the circuit board, and the circuit board outputs a notification message to the backend monitoring server when the door sensor detects opening of the door plate.

6. The cabinet with AED light signal display as claimed in claim 3, wherein an alarm display panel is disposed on the cabinet body and displays an area plan displaying alert lights respectively corresponding to actual positions of alarm transmitters, when any one of the alarm transmitters is activated, an alert signal output therefrom is received by the wireless signal transceiver, and the circuit board activates the alarm display panel, enabling the alert light corresponding to the alarm transmitter which is activated to emit light.

7. The cabinet with AED light signal display as claimed in claim 3, wherein the circuit board is further connected to a temperature and humidity sensor detecting temperature and humidity in the cabinet body and transmitting the same to the backend monitoring server through the wireless signal transceiver.

8. The cabinet with AED light signal display as claimed in claim 3, wherein the circuit board is further connected to an audio sensor detecting a sound in the cabinet body and transmitting a signal of the sound to the backend monitoring server through the wireless signal transceiver.

9. The cabinet with AED light signal display as claimed in claim 8, wherein a carbon monoxide sensor is disposed in the exterior of the cabinet body and outputs an alert sound when a carbon monoxide concentration exceeding a predetermined level is detected, and the audio sensor detects the alert sound and transmits a signal corresponding thereto to the backend monitoring server.

10. The cabinet with AED light signal display as claimed in claim 1, wherein the cabinet body further comprises a power module electrically connected to power mains and the circuit board, the power mains power the circuit board through the power module, and the power module outputs electric power in the event of a power failure.

* * * * *